United States Patent
Lolley

(10) Patent No.: US 10,842,138 B1
(45) Date of Patent: Nov. 24, 2020

(54) METHOD, DEVICE, AND SYSTEM FOR USE WITH INSECT LARVAE

(71) Applicant: Insecticycle LLC, Fort Collins, CO (US)

(72) Inventor: Michael D. Lolley, Fort Collins, CO (US)

(73) Assignee: Insecticycle LLC, Fort Collins, CO (US)

( * ) Notice: Subject to any disclaimer, the term of this patent is extended or adjusted under 35 U.S.C. 154(b) by 151 days.

(21) Appl. No.: 16/051,011

(22) Filed: Jul. 31, 2018

Related U.S. Application Data

(60) Provisional application No. 62/540,310, filed on Aug. 2, 2017.

(51) Int. Cl.
| | |
|---|---|
| A01K 67/033 | (2006.01) |
| A01K 29/00 | (2006.01) |
| C05F 3/06 | (2006.01) |
| C05F 17/05 | (2020.01) |

(52) U.S. Cl.
CPC .......... *A01K 67/033* (2013.01); *A01K 29/005* (2013.01); *C05F 3/06* (2013.01); *C05F 17/05* (2020.01)

(58) Field of Classification Search
CPC ........................... A01K 67/033; A01K 29/005
See application file for complete search history.

(56) References Cited

U.S. PATENT DOCUMENTS

| | | | |
|---|---|---|---|
| 5,351,643 A | 10/1994 | Hughes | |
| 5,618,574 A | 4/1997 | Bunch | |
| 5,819,685 A | 10/1998 | Kappelt et al. | |
| 6,474,259 B1* | 11/2002 | Gaugler | A01K 67/033 119/6.7 |
| 6,938,574 B2 | 9/2005 | Zhang | |
| 8,322,302 B2 | 12/2012 | Chang | |
| 8,322,303 B2 | 12/2012 | Chang | |
| 8,647,686 B1 | 2/2014 | Rojas et al. | |
| 8,733,284 B2 | 5/2014 | Courtright | |
| 8,895,767 B2 | 11/2014 | Araneda Herrera | |
| 9,462,795 B2 | 10/2016 | Chin | |
| 9,629,339 B2 | 4/2017 | Newton et al. | |

(Continued)

FOREIGN PATENT DOCUMENTS

| | | |
|---|---|---|
| WO | 2012115959 A2 | 8/2012 |
| WO | 2014137179 A1 | 9/2014 |

(Continued)

OTHER PUBLICATIONS

Park, Black Soldier Fly Larvae Manual, University of Massachusetts—Amherst, ScholarWorks@UMass Amherst, 2016, pp. 1-14.

*Primary Examiner* — Monica L Barlow

(74) *Attorney, Agent, or Firm* — MacMillan, Sobanski & Todd, LLC

(57) ABSTRACT

Provided are methods, devices and systems for cultivating insect larvae and processing organic material. Exemplary systems and methods provide an arrangement of shelves containing trays for larvae cultivation and frass collection. The shelves are maintained in a controlled environment and are adapted to receive a feedstock comprising organic material for conversion into insect biomass. A system for continuous harvesting of larvae and frass is provided.

13 Claims, 4 Drawing Sheets

(56) References Cited

U.S. PATENT DOCUMENTS

| | | |
|---|---|---|
| 9,642,344 B2 | 5/2017 | Unger |
| 10,051,845 B1 | 8/2018 | Massaro et al. |
| 10,058,080 B2 | 8/2018 | Leo |
| 10,405,528 B2 | 9/2019 | Comparat et al. |
| 2002/0177219 A1 | 11/2002 | Olivier |
| 2003/0143728 A1 | 7/2003 | Olivier |
| 2011/0139075 A1* | 6/2011 | Shapiro Ilan ........ A01K 67/033 119/6.5 |
| 2011/0174222 A1 | 7/2011 | Lee |
| 2012/0187041 A1 | 7/2012 | Popa et al. |
| 2013/0319334 A1 | 12/2013 | Newton et al. |
| 2015/0122182 A1 | 5/2015 | Aldana et al. |
| 2015/0164109 A1 | 6/2015 | Ruben |
| 2015/0245569 A1 | 9/2015 | Villamar |
| 2015/0296760 A1 | 10/2015 | Perednia |
| 2015/0374005 A1 | 12/2015 | Arsiwalla et al. |
| 2016/0219887 A1 | 8/2016 | Vickerson et al. |
| 2017/0202191 A1 | 7/2017 | Marchant et al. |
| 2018/0007874 A1 | 1/2018 | Hall et al. |
| 2018/0092339 A1 | 4/2018 | Massaro et al. |
| 2018/0116184 A1* | 5/2018 | Kemp .................... A01K 61/59 |
| 2019/0191678 A1* | 6/2019 | Alrayya ................ A23K 50/90 |

FOREIGN PATENT DOCUMENTS

| | | |
|---|---|---|
| WO | 2015173450 A1 | 11/2015 |
| WO | 2016005296 A1 | 1/2016 |
| WO | 2016166471 A1 | 10/2016 |

\* cited by examiner

US 10,842,138 B1

METHOD, DEVICE, AND SYSTEM FOR USE WITH INSECT LARVAE

CROSS-REFERENCE TO RELATED APPLICATIONS

This application claims the benefit of U.S. application No. 62/540,310, filed Aug. 2, 2017, which is herein incorporated by reference in the entirety.

BACKGROUND

Insects can be a useful resource and recent activity has focused on ways humans can benefit from the industrialization of select species. Some applications have been proposed as a sustainable means of recycling organic materials, and to generate animal feed and fertilizer. However, several technological challenges exist that can make a large scale operation difficult to manage and maintain continuously.

An exemplary species of interest is the black soldier fly, *Hermetia illucens*, whose larvae are known feeders of a wide variety of organic materials. Black soldier fly larvae are well suited for industrialization, having behavioral characteristics which can be manipulated in ways that facilitate cultivation and large population growth. Systems can be created for automated activities such as feeding, harvesting and reproduction. Current literature describes some conditions under which larvae thrive but lacks many details on supporting and maintaining these conditions continuously, as well as creating automatic systems to actively control these conditions for efficient management. Many systems require several physical actions to be manually repeated on a batch style process, which can be inefficient and labor intensive.

Large scale insect cultivation can contribute to sustainable production of agricultural products as new advancements will serve to increase the operational ability of these systems. Thus, there is a need for improved systems and methods for cultivating insect larvae.

SUMMARY

A system and method is provided for containing and rearing of insect larvae for the processing of organic material. The system incorporates an arrangement of shelves containing trays for larvae cultivation and frass collection. The shelves are maintained in a controlled environment and adapted to receive applications of prepared feedstock for conversion into insect biomass. A system for harvesting of larvae and frass is also provided.

DETAILED DESCRIPTION

Figure 1:
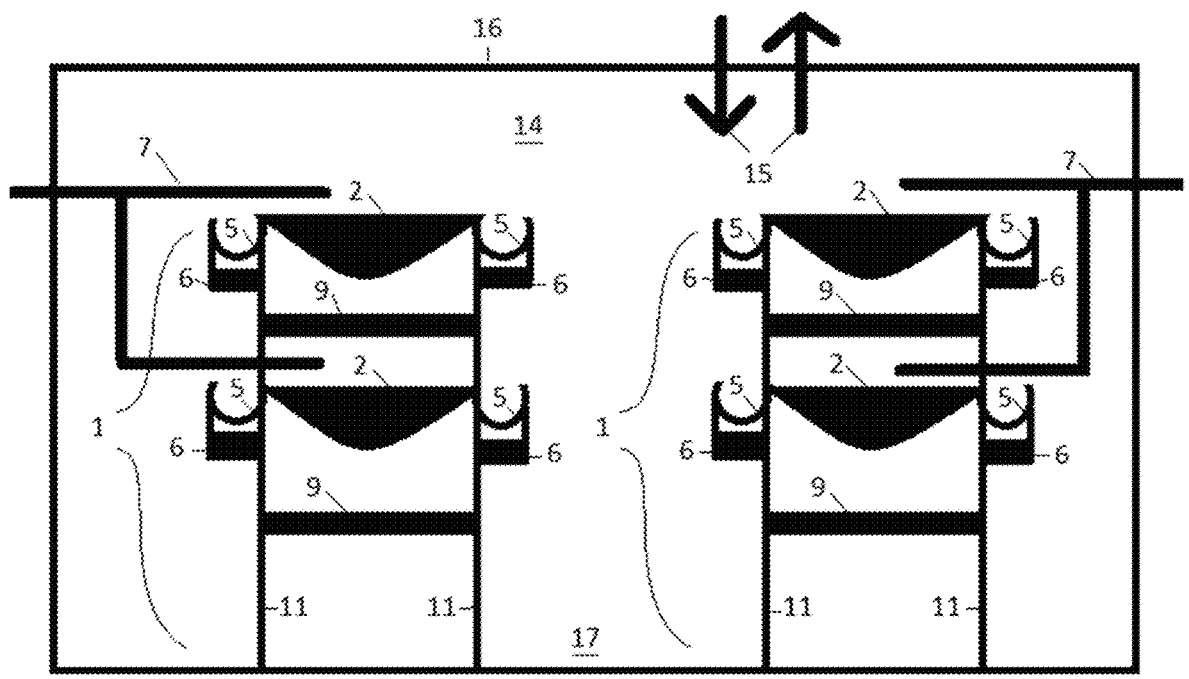
FIG. 1 shows an example of a larvae cultivation system and surrounding structure.
Figure 2:
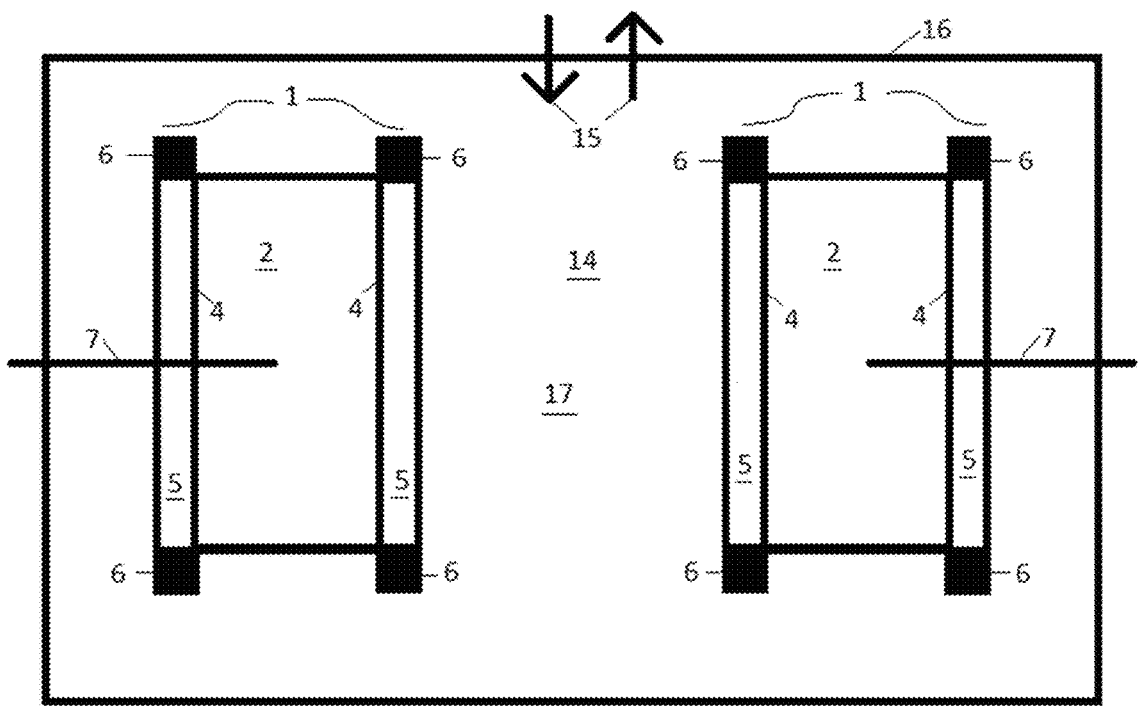
FIG. 2 shows the larvae cultivation system and structure from above.

As discussed in detail below, some of the embodiments of the invention include systems for containing and tending insect larvae for the continuous processing of organic material. Insect larvae cultivation structures and growth conditions can be manipulated to increase the productivity and efficiency of insect larvae cultivation.

Described herein are systems and methods for larvae cultivation. The embodiment pictured in FIGS. 1-4 shows larvae trays 2 which may contain a dense population of larvae, known as a colony 19. Beneath each larvae tray 2 is a frass tray 9 for collecting frass 10. The trays 2, 9 are organized vertically in shelves 1 to more efficiently use floor space. The larvae trays 2 feature a porous bottom surface 3, often a wire mesh screen, which supports the larvae colony 19, and spans across a width of the larvae tray 2. The screen 3 is suspended in place above the frass tray 9 by the use of screen support pieces 12, 13. The support pieces may be joined together as one solid unit, with the screen material 3 embedded in between the upper 13 and lower 12 support pieces in such a way that the screen 3 is fixed firmly in place, suspended over the frass tray 9, and the shape of the bottom surface 3 is formed with a curve or angle on one or more sides facing upwards. Frass trays 9 may comprise a flat or curved solid surface which collects frass 10 as it passes through the larvae tray bottom 3. Each tray 2, 9 rests upon the tray supporting framework 18 which connects to the vertical supports 11 to create a shelf 1.

The number of trays 2, 9 and shelves 1 in a structure 16 may vary as well as the spacing around the shelves. The larvae tray 2 may be wide enough to ensure that either edge 4 of the tray can be accessed by mature larvae 20 seeking to exit the larvae colony 19. In some embodiments, the trays 2, 9 may be between about 1-5 feet wide, about 2-4 feet wide or about 3 feet wide. In some embodiments, larvae trays 2 and frass trays 9 can be removed from the shelf 1 as one piece for added ease. In some embodiments, a frass tray 9 may be angled or may be curved to provide for easier frass 10 collection. Shelves 1 may be modular to easily be assembled or broken down depending on space and process needs. The shelves 1 are arranged to receive controlled applications of food 8 from a food delivery system shown in FIGS. 5-6.

The shelves 1 are housed within a structure 16 providing an environment 14 for the larvae in the colonies 19 to thrive. Conditions such as temperature, humidity and airflow within the contained environment 14 may be manipulated to enhance the efficiency of the system. The equipment 15 used may include items such as humidifiers, air conditioning systems, fans, filters, heaters and other ways of manipulating the environmental conditions within the structure 16. In some embodiments shelves 1 are arranged adjacent to a walkway 17 in order to allow a person to harvest larvae 19, 20 and frass 10. In other embodiments, chutes, angled surfaces and mechanical structures may automate one or more aspects of harvesting larvae 19, 20 or frass 10.

In an embodiment, the trays 2, 9 may be organized so that a frass tray 9 separates each larvae tray 2 in the vertical order and a larvae tray 2 is always placed above and paired with a frass tray 9. In this embodiment, vertical space in between a bottom part of a frass tray 9 from a first tray set is about 2 or more inches above an upper part of a larvae tray 2 of another tray set to allow feeding tubes 7 or other devices to be placed between the pairs of trays 2, 9. Food 8 may be delivered via feeding tubes 7 continuously or periodically in timed intervals. Feeding tubes 7 do not make contact with the tray 2 so that food 8 may fall freely onto the larvae colony 19.

In some embodiments, the feeding tube delivers food 8 to the center portion of the larvae tray 2, wherein the center portion is 50% of the width along the length of the centerline. In some embodiments, one feeding tube 7 delivers food 8 directly above the center of the larvae colony 19 of a single tray. In some embodiments, a plurality of feeding tubes 7 delivers food 8 from points evenly spaced above the larvae trays 2 at a plurality of openings along a lengthwise centerline above the deepest part of the larvae tray 2.

The frass trays 9 are positioned underneath each larvae tray 2 to facilitate collection of frass 10. Frass 10 may emerge from the larvae tray 2 as a dry, solid material. As it is produced, the frass 10 passes through the spaces in the screen bottom 3 for collection. This arrangement enables the continuous separation of frass 10 from the larvae 19 and helps maintain a consistent volume of material in the larvae tray 2. This allows larvae 19 contained in the larvae tray 2 to feed without interruption.

Figure 3:
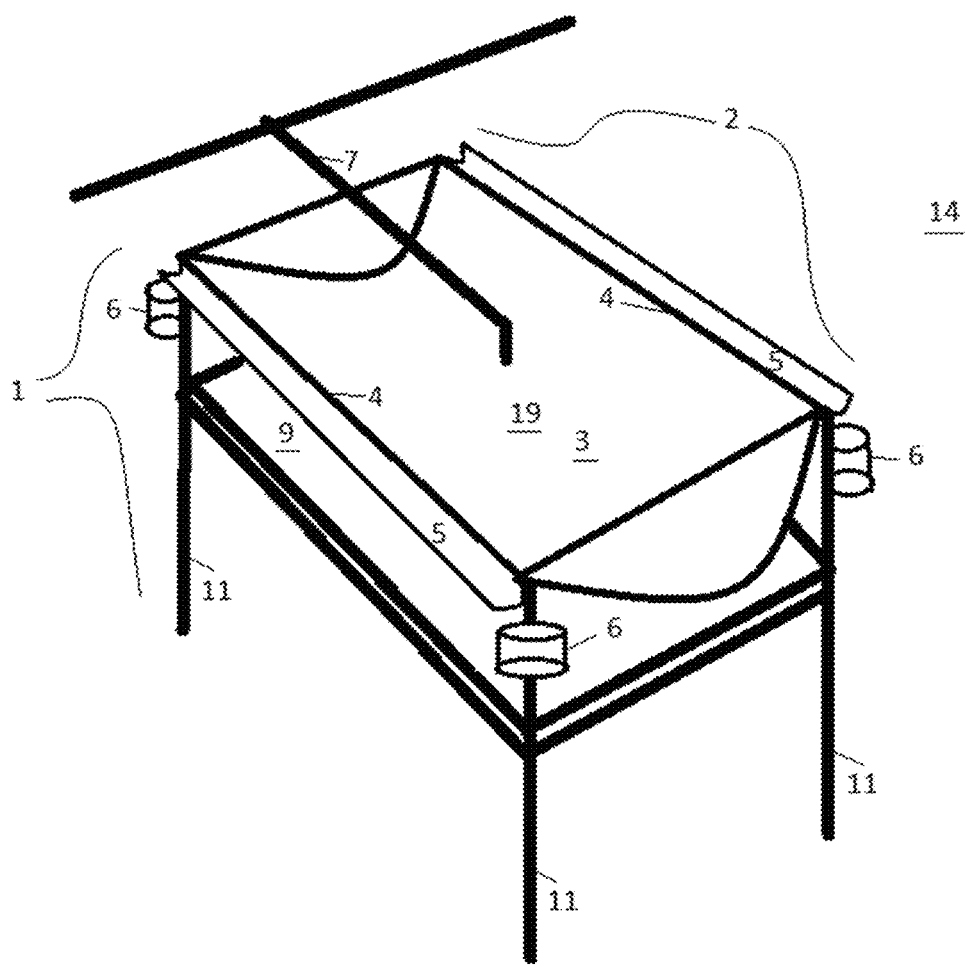
FIG. 3 shows a perspective view of an embodiment of a larvae tray.
Figure 4:
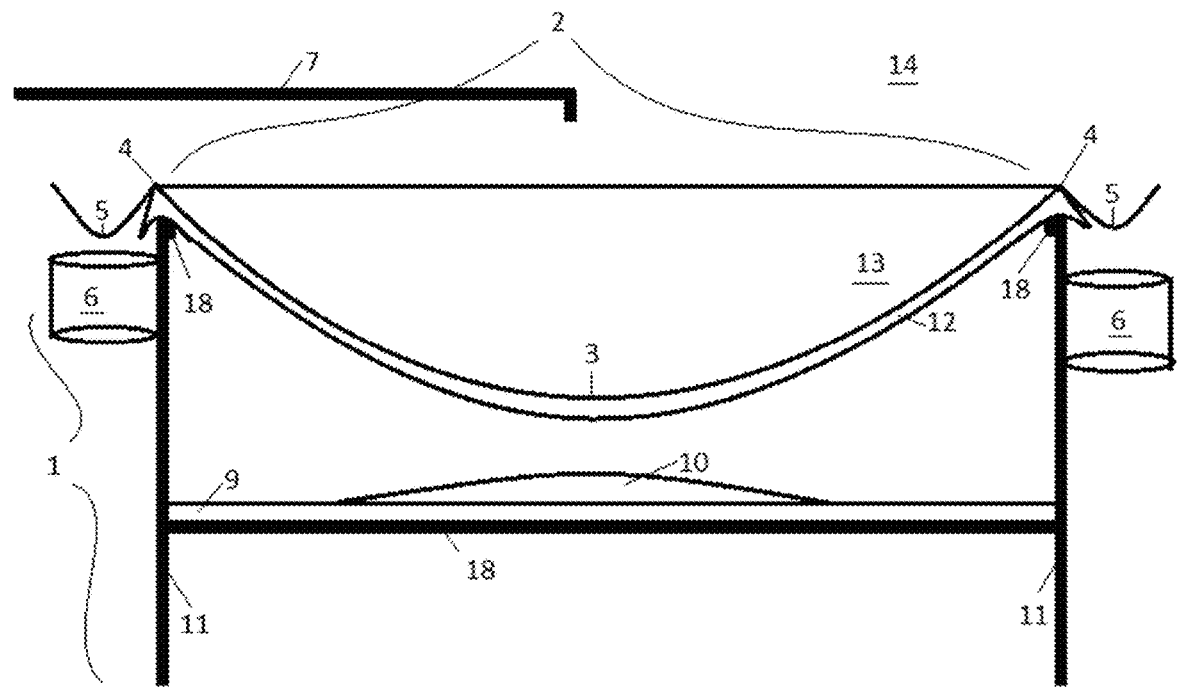
FIG. 4 shows a cutaway elevational view of a larvae tray as viewed from the end.

FIGS. 3 and 4 depict a larvae tray 2 in closer detail. In an embodiment, each larvae colony 19 is fed by dispensing a metered dose of food 8 into the center of the larvae trays 2 several times daily at regularly timed intervals, promoting feeding activity by juvenile larvae 25 in the larvae colony 19. Dose size and interval may vary depending on the condition of the larvae colony 19 and of the food 8 itself. Conditions within the larvae colony 19 before feeding may consist of low relative humidity and with food 8 from the previous feeding having been entirely consumed. As the food 8 first makes contact with the larvae colony 19, juvenile larvae 25 seeking moisture and nutrients orient themselves toward the food 8, while pushing frass 10 and any uneaten material towards the outer edges 4 and through the screen bottom 3. As the food 8 is consumed, the juvenile larvae 25 will increase in density surrounding the food 8, consuming the majority of the food 8. Once the food 8 is consumed and moisture levels have dropped, another feeding dose may be given. During the feeding activity, mature larvae 20 seek to escape the active juvenile larvae 25 in the colony 19 by crawling towards the edge 4 of the larvae tray 2. On either side of the larvae trays 2 are collection chutes 5 which gather mature larvae 20 as they crawl over the edge 4.

After some time, the larvae population 19, 25 within the trays will decrease from the amount of mature larvae 20 exiting. To keep active population numbers steady, the larvae trays 2 are periodically supplemented by adding young juvenile larvae 25 produced through breeding adult flies. Depth of the larvae colony 19 can be used to measure size of the colony 19. A depth of between 3-6 inches is preferred however greater depths may be used unless conditions become unstable or measurements deviate from healthy colony conditions with regard to factors such as: moisture level, temperature, pH, food consumption rate, carbon dioxide level, and oxygen level. Measurements may be taken intermittently, periodically, or continuously to assess environmental conditions within the colony 19 and of the controlled environment 14 to maintain conditions within the preferred ranges and correct deviations promptly. In some embodiments the larvae 19, 20, 25 are able to tolerate conditions that are outside the ranges of normal operation for prolonged periods of time. In some embodiments, deviations of 30% of the preferred ranges may be tolerated for a duration not exceeding 10% of every 24 hour period.

In the embodiment of FIGS. 1-4, each larvae tray bottom 3 is formed by screen mesh which can be curved or angled upwards on the ends, creating a shallow trough for the larvae colony 19 to rest in. This tray 2 may continue for the length of the shelf 1 or be divided into sections for easier control of the populations in each colony 19. At each end of the larvae tray 2 are flat, vertical surfaces formed by the upper support pieces 13, forming barriers which are as tall, or taller than, the edge 4 of the tray, to prevent the larvae 19, 20, 25 from escaping past the larvae tray 2 end.

The porous nature of the material and size range of the holes in the screen bottom 3 allow for larvae 19, 20, 25 to be contained within the tray 2, and solid frass 10 to pass through. In some embodiments, holes can be about 0.6 to 1 mm in size creating a space large enough to allow frass 10 to pass but not larvae 19, 20, 25. In some embodiments, holes, perforations, gaps, or slots have a width 0.1-5.0 mm. In some embodiments, the width is determined by the size of juvenile larvae 25 introduced into the colony 19, with widths equal to or less than 90% of the smaller of the width or length of introduced juvenile larvae 25. In some embodiments, the total open space of the porous material is between 20-80%, 30-70%, or about 60%. In some embodiments the larvae tray bottom 3 consists essentially of the porous material. In some embodiments the bottom 3 and one or more sides consist essentially of the porous material. Larvae 19, 20, 26 movement and feeding activity forces frass 10 through the holes. This sifting action is used to reduce the amount of frass 10 and other solid material in the tray 2. A further advantage is that the mesh or screen promotes air exchange with the controlled environment 14 and better maintains environmental variables within the larvae colony 19. These variables may include moisture levels, temperature, pH, food availability, carbon dioxide levels, and oxygen levels.

Figure 6:
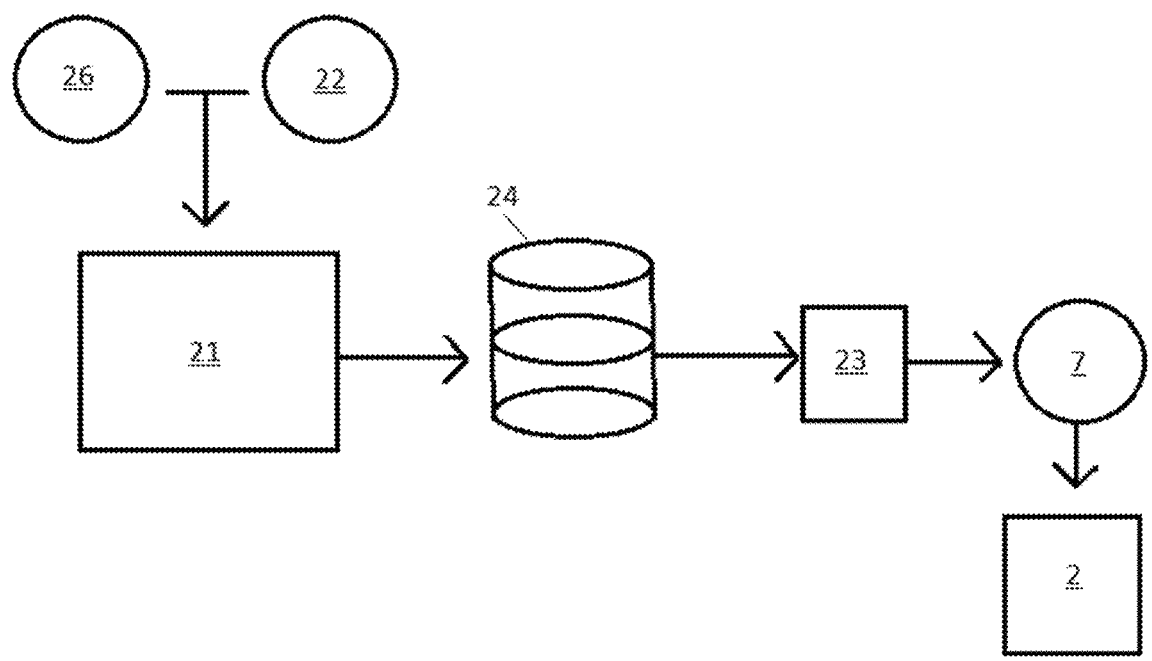
FIG. 6 depicts materials passing through a feed mixing and delivery system.

In an embodiment, a food delivery system mixes feedstock 26 and additional materials 22 into food 8 and controls the application of food 8 and automatically delivers food 8 to the larvae trays 2. FIG. 6 depicts an embodiment of a food preparation and delivery system. Feedstock 26 is mixed with water and homogenized with mechanical blending equipment 21 to a viscous slurry-like consistency to form prepared food 8. Additional materials 22 may be added to the feedstock 8 to adjust pH, nutrient content, solids and other characteristics desired for improved feeding and to manipulate qualities of the produced larvae 19, 20, 25. A slurry with substantially uniform viscosity is preferred to enhance feeding action and increase processing speed. The viscous food 8 can be contained within a vessel 24 and transported by a pump 23 through feed lines 7 running from the pump 23 to the larvae trays 2. As the larvae 19, 25 rapidly consume the food 8, any uneaten food particles as well as larvae droppings 10 may pass through the tray bottom 3. Frass 10 may accumulate underneath in a separate frass tray 9 and be harvested regularly. Large particles of food 8 may occasionally accumulate on top of the larvae tray 2 surface without passing through and can be manually removed.

In some embodiments, under the conditions provided by the controlled environment 14, tray 2, 9 design, and food delivery system, mature larvae 20 exit the colony 19 by crawling over the edge 4 of the tray 2 and into the collection chute 5. By maintaining continuous or frequent feeding activity, juvenile larvae 25 may be drawn towards the center of the larvae tray 2, away from the edges 4 of the larvae tray 2. In some embodiments, the frequency and central location of food delivery to the larvae tray 2 promotes mature larvae 20 to move up the sides of the tray 2 and away from the feeding activity in the center, creating a separation of mature 20 and juvenile larvae 25 of the colony 19. Chutes 5 may direct mature larvae 20 into the collection receptacle 6 for gathering. Frass 10 may simultaneously be collected in the frass trays 9 underneath the larvae 19. In larger operations the frass trays 9 may include a conveyor mechanism that further assists the collection process.

Figure 5:
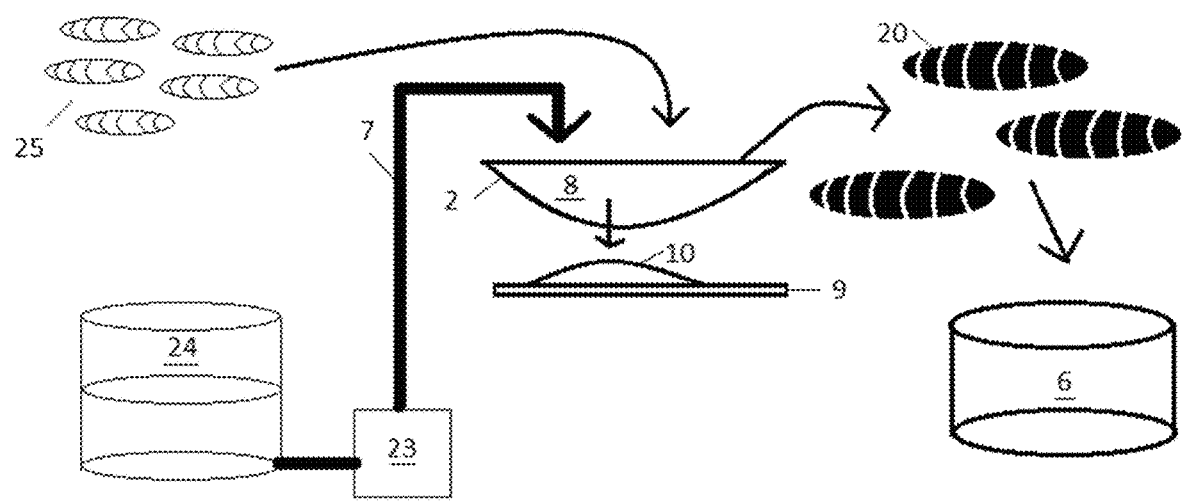
FIG. 5 depicts the flow of various materials through the system.

As shown in FIG. 5 and discussed above, juvenile larvae 25 are added and mature larvae 20 are harvested to and from the larvae tray 2, respectively. Under these conditions, the feeding and harvesting cycle described above may be repeated and maintained indefinitely and continuously with minimal interference from activities such as the exchange of materials including effluent, growth substrate, food 8, water, larvae 19, 20, 25, and frass 10. In some embodiments juvenile larvae 25 are added periodically every 1-20 days in quantities within 25% of the number of mature larvae 20 harvested over the 1-20 day period.

Figure 7:
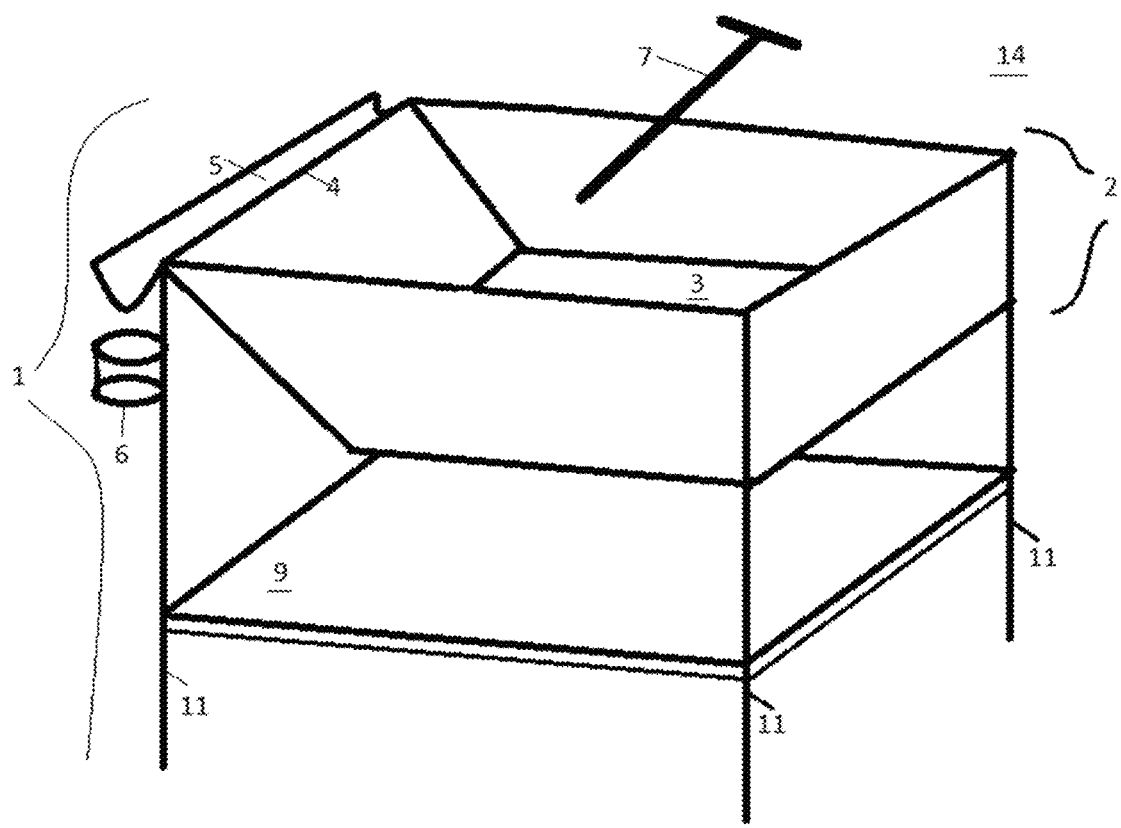
FIG. 7 shows another embodiment of a larvae tray.

FIG. 7 shows an alternate embodiment showing a larvae tray 2 in which a collection chute 5 is adjacent a terminal edge 4. A harvest ramp extends to the terminal edge 4, adjacent the chute 5, from a porous bottom support surface 3. In this embodiment the sides of the larvae tray 2 may be made of a different material than the bottom support surface 3, and the sides may be a solid, non-porous material.

In an exemplary embodiment, the insect larvae 19, 20, 25 is a black soldier fly, *Hermetia illuicens*. Juvenile larvae 25 may be transferred into a larvae tray 2 or cultivation structure approximately 7-21 days after hatching or upon reaching a length of about 0.5 cm. Moist food 8 and a suitable growth environment may be provided. The larvae colony 19 forms a mass in which 50-100% of the mass comprises juvenile larvae 25. Moisture and humidity levels of the controlled environment 14 around the larvae tray 2 may be lower than moisture levels within the colony 19, providing a moisture differential. A moisture differential of about 5-85% between the controlled environment 14 and the colony 19 may be maintained by mechanically lowering humidity levels in the controlled environment 14, by the addition of food 8, and by larval 19, 25 respiratory and metabolic processes. Juvenile larvae 25 may grow for about 14-65 days or until reaching mature size at a length of about 2 cm.

In some embodiments, the controlled environment 14 has a relative humidity level of less than 40 percent. In some embodiments, the humidity level is maintained at a level of 5-40%, 5-35%, 10-35%, 15-25%, 25-35%, or 25-30%. In some embodiments, the controlled environment 14 has a relative humidity level of less than 40% for at least 90% of every 24 hour period. Addition of water directly to the colony 19 may not be required. In some embodiments, no water is added directly to the colony 19 at any time, and no effluent is produced. In some embodiments the humidity level is altered to provide an environmental cue to stimulate a behavioral change in the larvae 19, 20, 25.

In some embodiments the feedstock 26 comprises one or more of: brewers grains, restaurant food waste, repurposed retail food, fruits, vegetables, grains, meat, dairy and or other organic byproducts. In some embodiments, the food 8 is supplemented with additives 22 to adjust pH to a level between about 3.0 to 9.0, about 5.0 to 8.5, about 6.0 to 8.0, or to about 7.0. In some embodiments, the feedstock 26 or food 8 is supplemented with additives 22 to produce a more nutritionally desirable larvae 19, 20, 25.

In some embodiments, delivering food 8 to the larvae tray 2 is performed periodically and regularly. In some embodiments, the food 8 is delivered several times an hour, once every hour, about once every 2 hours, once every 4 hours, once every 6 hours, once every 8 hours, once every 24 hours, once every 48 hours, once every 36 hours, or once every 12 hours. In some embodiments, the amount of food 8 delivered per day is approximately 10-50% of the mass of the larvae colony 19. In some embodiments, the amount of food 8 delivered per feeding is approximately 1-25% of the mass of the larvae colony 19. In some embodiments, the amount of food 8 delivered per feeding cycle is about 20-30%, 15-25%, or 10-25% of the mass of the larvae colony 19.

In some embodiments, a larvae colony 19 is maintained in the manner described, without interruption, in the larvae tray 2 for a period of at least 3 months, 6 months, 12 months, 18 months, 24 months, 36 months, or 48 months. In some embodiments a larvae colony 19 is maintained, without interruption, in a mass containing at least 50 individual larvae, wherein the larvae colony 19 remains at a steady size within 25% variance by weight, in the larvae tray 2 for a period of 3-6 months, 4-10 months, 6-12 months, 6-18 months, or 12-24 months. In some embodiments, the larvae tray 2 attaches to a scale on the supporting rack or shelf 1 to measure an approximate weight of the larvae colony 19.

In some embodiments a larvae colony 19 is maintained in a controlled environment 14 at a temperature of 75-95 degrees Fahrenheit. In some embodiments a larvae colony 19 is maintained in a controlled environment 14 at a temperature of 60-80, 75-90, 85-95, or 80-90 degrees Fahrenheit. In some embodiments a continuous airflow is maintained past the larvae trays 2 containing the larvae colony 19 at a rate sufficient enough to facilitate air exchange and maintenance of environmental cues.

In some embodiments, mature larvae 20 display behavioral traits that are separate from those of juvenile larvae 25, due to different needs of the individual during certain stages of development. In some embodiments, environmental cues such as ramp position and food location may direct migration of mature larvae 20 from the colony 19, promoting mature larvae 20 to exit the tray 2, and drop into the collection chutes 5. In some embodiments, regulation of environmental cues, such as increasing feeding rate to increase feeding activity in the colony 19, can signal the juvenile larvae 25 to remain within the colony 19 and gather in a center region of the larvae tray 2. In some embodiments, a humidity differential is maintained to further distinguish between the center region of the larvae tray 2, within the colony 19, and an edge 4 area at, or adjacent to, a collection chute 5. In some embodiments, the humidity is lower at the edge 4 area and higher in the colony 19, with a relative humidity at an edge 4 area of about 35% or less and a relative humidity within the colony 19 between about 40-100%.

In some embodiments, a perimeter of the larvae tray 2 is substantially rectangular, and the porous bottom surface 3 extends substantially contiguously from one side and across to an opposite side of the rectangle, forming the bottom of the tray 3 and forming a surface which curves or angles upwards to adjoin the terminal edge 4 along the two opposites sides of the rectangle. In some embodiments, a perimeter of the larvae tray 2 is substantially rectangular, and the porous surface 3 extends and meets the terminal edge 4 along the entirety of at least two opposites sides of the rectangle. In some embodiments, the porous surface 3 extends and meets the terminal edge 4 along a portion of a side. In some embodiments, the porous surface 3 extends and meets the terminal edge 4 along the entirety of one side.

In some embodiments, a harvest ramp is formed by a side of the larvae tray 2, wherein the harvest ramp extends from the tray center region to a terminal edge 4 and a collection chute 5 is adjacent the terminal edge 4. The ramp has a gradual angle adjacent the terminal edge 4 adapted to permit mature larvae 20 movement up the ramp, and a transition to the collection chute 5 at the terminal edge 4 is steep, to permit mature larvae 20 movement from the ramp to the chute 5 and prevent larvae 19, 20, 25 movement from the chute 5 to the ramp. In an embodiment the steep drop off at the terminal edge 4 is angled about 90 degrees, or is greater than about 60 degrees.

In some embodiments, the porous bottom surface 3 formed from a screen is held or embedded in place by supporting end pieces 12, 13 and the supporting pieces 12, 13 prevent the larvae 19, 20, 25 from escaping out of the ends of the larvae tray 2 which do not adjoin or lie along the terminal edge 4. In some embodiments, the screen supporting pieces 12, 13 rest upon shelf supports 18 to suspend and hold the larvae tray 2 in place. In some embodiments the porous screen bottom 3 prevents larvae 19, 20, 25 from passing through the bottom 3 and comprises a polyester-coated or non-coated wire mesh, wherein a wire diameter is between about 0.05 mm to about 2.00 mm, wherein a gap between wires is between about 0.10 mm to about 1.00 mm, and wherein openings in the porous screen material comprise 40-80% of surface area of the porous screen material.

In some embodiments, a perimeter of the larvae tray 2 is substantially rectangular, with a length and a width. In some embodiments, the length is 0.5 to 4 times greater than the width. In some embodiments, the width is between 20-100 cm, 50-70 cm, or about 60 cm. In some embodiments, food 8 is delivered to a center portion of the larvae colony 19, wherein the center portion is a region adjacent a centerline through the larvae tray 2, and offset from the centerline by no more than 30% of the width of the larvae tray 2. In some embodiments, the larvae colony 19 is maintained in a center portion of the larvae tray 2 and 75-100% of juvenile larvae 25 are within 50 cm of a centerline through the larvae tray 2, parallel to a terminal edge 4.

Approximating language, as used herein throughout the specification and claims, may be applied to modify any quantitative representation that could permissibly vary without resulting in a change in the basic function to which it is related. Accordingly, a value modified by a term or terms, such as "about", and "substantially" is not to be limited to the precise value specified. In some instances, the approximating language may correspond to the precision of an instrument for measuring the value. Here and throughout the specification and claims, range limitations may be combined and/or interchanged, such ranges are identified and include all the sub-ranges contained therein unless context or language indicates otherwise.

In the specification and the claims, the singular forms "a", "an" and "the" include plural referents unless the context clearly dictates otherwise. As used herein, the term "or" is not meant to be exclusive and refers to at least one of the referenced components being present and includes instances in which a combination of the referenced components may be present, unless the context clearly dictates otherwise.

The terms and expressions which have been employed are used as terms of description and not of limitation. Whenever a range is given in the specification, all intermediate ranges and subranges, as well as all individual values included in the ranges given are intended to be included in the disclosure. It should be understood that, although the present invention has been specifically disclosed by particular embodiments and examples, optional features, modification and variation of the concepts herein disclosed may be used by those skilled in the art, and such modifications and variations are considered to be within the scope of the invention as defined by the appended claims.

APPENDIX A

1. Shelf—Freestanding support structure used to hold multiple sets of larvae and frass trays in a vertical column. In some embodiments, the shelf is assembled by joining support rails to legs.
2. Larvae tray—The structure used to support the larvae. In some embodiments, the larvae tray is a curved, shallow structure which rests on the shelf support rails, and the total depth of the tray from the bottom of the curve to the top of the upper support piece is approx 6 inches.
3. Porous bottom surface—Porous semi rigid surface that forms the bottom of the larvae tray. This serves to suspend the larvae over the frass tray and allows for maximum aeration surrounding the larvae colony. An exemplary porous bottom surface has a screen constructed of polyester coated wire mesh, having a wire diameter of about 0.2 mm, with the size of space between wires of about 0.8 mm and a total open space of about 60%. This size is large enough to provide a surface which is porous to frass particles, yet with gaps small enough that larvae past a certain point of development will not get through. The porous semi rigid surface may be mesh, webbing, a slotted material, a grate, or screen material and may be constructed of stainless steel, plastic, treated fabric, or other materials suitable for handling food and organic products.
4. Edge—Section of the larvae tray at the top of at least one side of the tray which encourages migration of mature larvae. Larvae seeking to crawl off will climb surfaces in order to get away from the colony and begin to pupate. The change in elevation provided by the ramp utilizes this climbing propensity to separate pre-pupae or mature larvae from immature, younger feeding larvae which have a propensity to remain the colony.
5. Collection chute—an area adjacent the larvae tray adapted to receive mature larvae from the larvae tray and inhibit movement of larvae from that area to the larvae tray. In some embodiments, the collection chute is a small U shaped trough on either side of the larvae tray which further directs the larvae into the harvest receptacle. Larvae can climb surfaces up to 45-55 degrees, steeper angles hinder or prevent larvae from ascending. The exit channel forms a shallow U shaped channel which is fully vertical on either side, promoting movement of the larvae toward the ends of the channel.
6. Harvest receptacle—receives and holds larvae migrating from collection chute until processing. As the larvae approach the end of the exit channel they fall into the receptacle and are held for collection.
7. Feeding tube—Tube which delivers feedstock to larvae tray. Food is mixed with water to form a feedstock having a viscosity and particle size which allows pumping of the mixture to the larvae trays via an automated feeding system.
8. Food—a viscous slurry containing moisture and nutrients. In some embodiments, food containing various organic materials like brewers grains or food waste is prepared. Before pumping it is brought to approximately a 90/10 water/solid mix. The pre mixing of the feedstock also ensures larvae get direct access to the nutrients and the frass particle size will easily pass through the screen after consumption. In some embodiments the food is a slurry having a viscosity in a range of about 10,000 to 100,000 centipoise (cP) at 70-80 degrees F.
9. Frass tray—A solid surface which collects frass as it passes thru the larvae tray. The frass can be gathered manually or mechanically. In some embodiments, the frass tray is angled or curved to facilitate collection. In some embodiments, the system further comprises an automated conveyor to facilitate mass harvesting.
10. Frass—The dry solid particulate matter which accumulates as a by-product of larvae feeding and excretion. This is a considerable by-product of the digestion process which has applications as a soil additive.
11. Shelf leg—supporting legs of the shelf that create a framework for the various trays to be supported.
12. Lower screen support—In some embodiments, a lower screen support holds the screen in place and supports larvae tray by resting on horizontal support pieces, joins with the upper screen support to form larvae tray and forming the curved shape of the ramps.
13. Upper screen support—In some embodiments, an upper screen support joins with the lower support to hold screen in place and provides a physical barrier to the larvae, forcing larvae to exit by crawling up the ramps on either side.
14. Controlled environment—the air conditions in the area surrounding the shelf units. In some embodiments, humidity is to be kept at 35% or below to control the movement of larvae in relation to their food. Air flow in the area should be sufficient enough to prevent anaerobic conditions from developing within the larvae colony. In some embodiments, a temperature range is between 80-90 degrees to support growth efficiency.
15. Environmental regulation mechanism—equipment used to control the environment. In some embodiments, it may include, but is not limited to: air conditioner, heater, humidifier, dehumidifier, fans, and filters.
16. Structure—building, tent or other physical structure that contains the environment and larvae system separate from the outside environment
17. Walkway—space for service workers to move and perform tasks.
18. Tray supporting framework—In some embodiments, a tray support is horizontal and attaches to legs of shelf to form supporting frameworks for trays to be placed.
19. Larvae colony—the dense mass of insect larvae which is in continuous feeding activity placed in the center of the larvae tray.
20. Mature larvae—larvae whose behavior and coloration is distinctively different from the larvae which make up the larvae colony. These larvae may seek to exit the colony and find a shelter to begin transformation into adult insects.
21. Blending equipment—In some embodiments, blending equipment is used to prepare food for delivery to the trays.
22. Additional materials—materials used to alter characteristics of the food to be more desirable for larvae production, preferably feed grade materials if the harvested mature larvae are for use in animal feed.
23. Pump—capable of moving the slurry through the feed lines in a controlled manner.
24. Vessel—used to hold the feedstock until needed.
25. Juvenile larvae—Larvae not yet fully grown, added periodically to larvae tray.
26. Feedstock—Starting material for preparation into food for larvae. May consist of brewers grains, restaurant waste, reclaimed retail food or any organic material suitable for use in feeding larvae.

What is claimed is:
1. A system for tending larvae and rearing juvenile larvae to mature larvae comprising:
   a harvest receptacle configured to receive mature larvae;
   a collection chute configured to transfer mature larvae to the harvest receptacle;
   at least one larvae tray for the containment and separation of juvenile larvae from frass, the larvae tray comprising:
      a bottom formed by a porous screen material adapted to support the larvae in a growth region and allow at least a portion of the frass to pass through the bottom;
      an uncovered top adapted to receive juvenile larvae and food; and
      a terminal edge separating the growth region from the collection chute;
         wherein at least a portion of the porous screen material further forms a surface which curves or angles upwards to adjoin at least a portion of the terminal edge;
         wherein an angle of the surface adjoining the terminal edge is between 5-55 degrees relative to a horizontal plane; and
         whereby the terminal edge permits movement by larvae from the growth region to the collection chute and prevents movement by larvae from the collection chute to the growth region; and
   at least one frass collection tray positioned below at least a portion of the larvae tray.

2. The system of claim 1, wherein a perimeter of the larvae tray is substantially rectangular, and wherein the surface extends and meets the terminal edge along two opposites sides of the rectangle.

3. The system of claim 2, wherein at least one feed line directs a flow of the food to points along a center midline region of the plurality of larvae trays.

4. The system of claim 1, wherein
   a plurality of trays are stacked vertically in layers and supported by a shelf;
   multiple shelves are placed in rows inside a structure, wherein the rows are separated by a walkway; and
   the inside of the structure has a controlled environment that is substantially controlled.

5. The system of claim 1 wherein a curvature or angle of the surface provides a directional cue for the larvae, wherein the directional cue signals movement of mature larvae toward the terminal edge, and wherein the directional cue prevents or deters juvenile larvae from approaching the terminal edge and escaping the larvae tray.

6. The system of claim 1, wherein the frass tray further comprises a conveyor belt to assist collection of frass.

7. The system of claim 1, wherein the porous screen material prevents larvae from passing through the bottom and comprises a wire mesh, wherein a wire diameter is between about 0.05 mm to about 2.00 mm, wherein a gap between wires is between about 0.10 mm to about 5.0 mm, and wherein openings in the porous screen material comprise 40-80% of surface area of the porous screen material.

8. The system of claim 1, wherein the porous screen material facilitates air exchange between a controlled environment and a larval colony comprised of juvenile larvae in the larvae tray, and wherein the air exchange is sufficient to prevent anaerobic conditions from being created in the larvae colony.

9. The system of claim 1, wherein the food is a slurry comprising water and solid organic material, and wherein the slurry has a viscosity in a range of about 10,000 to 100,000 cP.

10. The system of claim 1, wherein at least one larvae tray is maintained within a controlled environment, wherein the controlled environment provides at least one environmental cue to regulate migration of larvae, and wherein the additional cue is selected from the group consisting of: humidity level, airflow, temperature, pH, food availability, and moisture content.

11. The system of claim 1, further comprising an end piece, wherein an edge of the porous screen material is fixed in place by the end piece, wherein the end piece forms a substantially vertical solid surface at a tray end, and wherein the end piece is a barrier to larvae movement, thereby preventing larvae from exiting the larvae tray at the tray end.

12. The system of claim 1, further comprising a pair of end pieces located on opposite ends of a larvae tray, wherein the pair of end pieces rest upon shelf supports, thereby suspending and holding the larvae tray in place on a shelf of a rack.

13. The system of claim 1, wherein the larvae is black soldier fly larvae.

* * * * *